United States Patent [19]  [11] 4,020,059
Maeda et al.  [45] Apr. 26, 1977

[54] PROCESS FOR PREPARING TERTIARY AMINES

[75] Inventors: Isamu Maeda; Hiroshi Koike, both of Takatsuki; Takashi Ohara, Nishinomiya, all of Japan

[73] Assignee: Nippon Shokubai Kagaku Kogyo Co., Ltd., Japan

[22] Filed: June 2, 1975

[21] Appl. No.: 582,822

[52] U.S. Cl. .................. 260/243 B; 260/244 R; 260/247; 260/252; 260/268 R; 260/293.51; 260/293.72; 260/293.82; 260/296 A; 260/309.6; 260/310 C; 260/310 D; 260/310 R; 260/313.1; 260/315; 260/319.1; 260/326.1; 260/329 AM; 260/563 R; 260/570.6; 260/570.8 R; 260/583 R

[51] Int. Cl.$^2$ .................................. C07D 295/00

[58] Field of Search ............. 260/243 B, 244, 247, 260/252, 268 R, 293.51, 293.72, 293.82, 315, 309.6, 326.1

[56] References Cited
UNITED STATES PATENTS 3,041,355   6/1962   Eugster et al. .................. 260/347.7

OTHER PUBLICATIONS

Bunnett et al., I, J. Am. Chem. Soc., vol. 71, pp. 1587–1589, (1949).
Bunnett et al., II, J. Am. Chem. Soc., vol. 75, pp. 985–987, (1953).
Bach, J. Org. Chem., vol. 33, pp. 1647–1649, (1968).
Mikhailova et al., Chem. Abst., vol. 80, item 59168(1974).
Houben Weyl, Methoden der Organischen Chemie, vol. 11/1, p. 649, (1957).

*Primary Examiner*—John D. Randolph
*Attorney, Agent, or Firm*—Wenderoth, Lind & Ponack

[57] ABSTRACT

A process for preparing tertiary amines, which comprises reacting a carbonyl compound with a formyl derivative of a secondary amine at a temperature of 100° to 350° C in the presence of water and/or a lower alcohol with or without further presence of a secondary amine.

16 Claims, No Drawings

PROCESS FOR PREPARING TERTIARY AMINES

This invention relates to a process for preparing tertiary amines, and more specifically, to a process for preparing tertiary amines by reacting a carbonyl compound with a formyl derivative of a secondary amine in the presence of water and/or a lower alcohol at a temperature of 100° to 350° C. The tertiary amines prepared by the process of this invention are useful as pharmaceutical intermediates. Quaternary ammonium salts prepared from the tertiary amines are useful as antibacterial agents, sterilizers, dye levelling and retarding agents, antistatic agents and textile softeners.

In the past, a method involving the alkylation of the nitrogen of a primary amine by suitable means has been employed to produce tertiary amines on an industrial scale. For example, alkyl dimethylamines can usually be prepared by reacting primary amines with a mixture of formic acid and formaldehyde, or by reacting primary amines with formaldehyde and hydrogen in the presence of a hydrogenation catalyst. [Methoden der Organischen Chemie, edited by Eugen Mueller, Band XI/1, Stickstoffverbindungen II, pages 641 to 643 and 650 to 651.] These methods, however, present various problems when applied industrially. For example, the primary amines are expensive, and the formic acid has a corrosive action on the equipment. Moreover, the activity of the hydrogenation catalyst is reduced.

It is an object of this invention to provide a process for preparing tertiary amines easily and at low cost without involving these defects of the prior art.

We made investigations about the production of tertiary amines by reacting carbonyl compounds with formyl derivatives of secondary amines with a view to achieving this object, and consequently found that water and/or lower alcohols contribute effectively to the above reaction. We have also discovered that when secondary amines are caused to be present in advance in the reaction system, the decomposition of the starting formyl derivatives of secondary amines is drastically inhibited, and the above reaction can afford tertiary amines with good efficiency.

Thus, according to this invention, there is provided a process for preparing tertiary amines, which comprises reacting a carbonyl compound with a formyl derivative of a secondary amine in the presence of water and/or a lower alcohol, or in the presence of water and/or a lower alcohol and a secondary amine, at a temperature of 100° to 350° C.

This reaction can be shown schematically as follows:

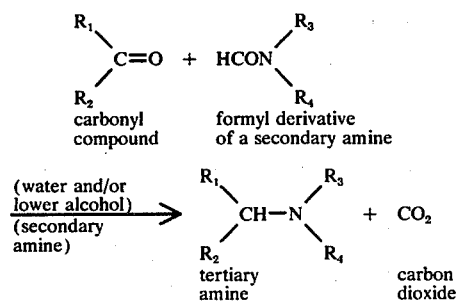

wherein $R_1$ is a hydrogen atom or an organic radical, and $R_2$, $R_3$ and $R_4$ each represent an organic radical.

According to the process of this invention, a mixture consisting of the carbonyl compound, the formyl derivative of secondary amine, water and/or lower alcohol, and if desired, the secondary amine, is heated at a temperature of 100° to 350° C. The resulting tertiary amine can be separated in a customary manner. In the process of this invention, the presence of water and/or a lower alcohol in the reaction system is essential. If water and/or a lower alcohol is not present in the reaction system, there is little or no proceeding of the reaction. Even if the reaction occurs, the selectivity to the tertiary amine is very low. When the secondary amine is caused to be present in the reaction system together with water and/or the lower alcohol, a merit is brought about of reducing the decomposition of the formyl derivative of the secondary amine. Since the decomposition of the formyl derivative of the secondary amine yields a secondary amine and carbon monoxide, this merit is of utmost significance in commercial operations.

The carbonyl compound used as a starting material in the process of this invention includes, for example, aliphatic aldehydes, alicyclic aldehydes, aromatic aldehydes, aliphatic ketones, aliphatic-aromatic ketones, aliphatic-heterocyclic ketones, aromatic ketones and alicyclic ketones.

Preferred aliphatic aldehydes are those of the general formula

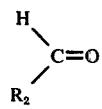

wherein $R_2$ is an aliphatic radical containing 1 to 40 carbon atoms.

Examples are ethanol, propanal, butanal, pentanal, hexanal, heptanal, octanal, nonanal, decanal, undecanal, dodecanal, tridecanal, tetradecanal, pentadecanal, hexadecanal, heptadecanal, octadecanal, nonadecanal, eicosanal, heneicosanal, docosanal, tricosanal, tetracosanal, pentacosanal, hexacosanal, heptacosanal, octacosanal, nonacosanal, triacontanal, hentriacontanal, ditriacontanal, tritriacontanal, tetratriacontanal, pentatriacontanal, hexatriacontanal, heptatriacontanal, octatriacontanal, nonatriacontanal, tetracontanal, hentetracontanal, pentanedial, hexanedial, octanedial, decanedial, dodecanedial, and straight-chain aliphatic aldehydes, such as straight chain oxoaldehydes obtained by the oxo-reaction of straight-chain monolefins containing 10 to 40 carbon atoms; and branded-chain aliphatic aldehydes such as 2-methylpropanal, 2-methylbutanal, 2-methylpentanal, 2-methylhexanal, 2-methylheptanal, 2-methyloctanal, 2-methylnonanal, 2-methyldecanal, 2-methylundecanal, 2-methyldodecanal, 2-methyltridecanal, 2-methyltetradecanal, 2-methylpentadecanal, 2-methylhexadecanal, 2-methylheptadecanal, 2-methyloctadecanal, 2-methylnonadecanal, 2-methyleicosanal, 2,2-dimethylpropanal 2-ethylbutanal, 2-ethylhexanal, 2-propylheptanal, 2-butyloctanal, 2-pentylnonanal, 2-hexyldecanal, 2-octyldodecanal and 2-methyloxoaldehyde mixtures obtained by the oxo-reaction of straight-chain monolefins containing 10 to 40 carbon atoms.

Preferred alicyclic aldehydes are those of the following general formula

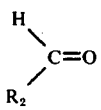

wherein $R_2$ is an alicyclic radical containing 5 to 20 carbon atoms.

Examples are cyclopentane-aldehyde, cyclohexane-aldehyde, cycloheptane-aldehyde, cyclooctane-aldehyde, cyclodecane-aldehyde, cyclododecane-aldehyde, cyclononadecane-aldehyde, cyclohexane-1,2-dialdehyde, cyclohexane-1,3-dialdehyde, cyclohexane-1,4-dialdehyde, 2-methylcyclohexane-aldehyde, 3-methylcyclohexane-aldehyde, 4-methylcyclohexane-aldehyde, and 4-methoxycyclohexane-aldehyde.

Preferred aromatic aldehydes are those of the general formula

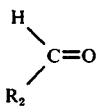

wherein $R_2$ is an aromatic radical.

Examples are benzaldehyde, o-phthalic aldehyde, m-phthalic aldehyde, p-phthalic aldehyde, α-naphthoic aldehyde, β-naphthoic aldehyde, o-tolualdehyde, m-tolualdehyde, p-tolualdehyde, o-anis-aldehyde, m-anisaldehyde, p-anisaldehyde, o-chlorobenzaldehyde, m-chlorobenzaldehyde, p-chlorobenzaldehyde, o-bromobenzaldehyde, m-bromobenzaldehyde, p-bromobenzaldehyde, 2,4-dimethoxybenzaldehyde, 3,4-dimethoxybenzaldehyde, o-nitrobenzaldehyde, m-nitrobenzaldehyde, p-nitrobenzaldehyde, p-dimethylaminobenzaldehyde, and cumic aldehyde.

Preferred aliphatic ketones are those of the general formula

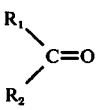

wherein $R_1$ and $R_2$ represent an aliphatic radical containing 1 to 20 carbon atoms.

Examples are 2-propanone, 2-butanone, pentanones, hexanones, heptanones, octanones, nonanones, decanones, undecanones, dodecanones, tridecanones, tetradecanones, pentadecanones, hexadecanones, heptadecanones, octadecanones, nonadecanones, eicosanones, heneicosanones, docosanones, tricosanones, tetracosanones, pentacosanones, hexacosanones, heptacosanones, octacosanones, nonacosanones, triacontanones, hentriacontanones, dotriacontanones, tritriacontanones, tetratriacontanones, pentatriacontanones, hexatriacontanones, heptatriacontanones, octatriacontanones, nonatriacontanones, tetracontanones, hentetracontanones, 4-methyl-2-pentanone, 2,4-dimethyl-3-pentanone, 2,6-dimethyl-4-heptanone, 1-phenyl-2-propanone, 1-(o-chloro)-phenyl-2-propanone, 1-(m-nitro)-phenyl-2-propanone, methyl cyclohexyl ketone, ketone mixtures obtained by the oxidation of straight-chain hydrocarbons containing 10 to 40 carbon atoms, and ketone mixtures obtained by the dehydrogenation of secondary alcohols containing 10 to 40 carbon atoms.

Preferred aliphatic-aromatic ketones are those of the general formula

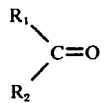

wherein $R_1$ is an aliphatic radical containing 1 to 20 carbon atoms and $R_2$ is an aromatic radical.

Examples are acetophenone, propiophenone, isobutyrophenone, isovalerophenone, laurophenone, β-acetonaphthone, p-chloroacetophenone, p-bromoacetophenone, p-methoxyacetophenone, p-methylacetophenone, m-nitroacetophenone, p-phenoxyacetophenone, and p-phenylacetophenone.

Preferred aliphatic-heterocyclic ketones are those of the general formula

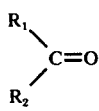

wherein $R_1$ is an aliphatic radical containing 1 to 20 carbon atoms, and $R_2$ is a heterocyclic radical.

Examples include α-acetothienone and α-propiothienone.

Preferred aromatic ketones are those of the following general formula

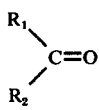

wherein $R_1$ and $R_2$ represent an aromatic radical.

Examples are benzophenone and fluorenone.

Preferred alicyclic ketones are those of the general formula

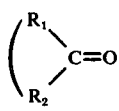

wherein $R_1 - R_2$ is a biradical containing 4 to 40 carbon atoms.

Examples are cyclopentanone, cyclohexanone, cycloheptanone, cyclooctanone, cyclodecanone, cyclododecanone, cyclopentadecanone, fenchone, menthone, 2-camphanone, 3-cholestanone, thujone, 2-methylcyclopentanone, 3-methylcyclopentanone, 2-methylcyclohexanone, 3-methylcyclohexanone, and 4-methylcyclohexanone.

The formyl derivative of a secondary amine used as a starting material in this invention includes, for example, formyl derivatives of aliphatic secondary amines and those of cyclic secondary amines.

Preferred formyl derivatives of aliphatic secondary amines are those of the general formula

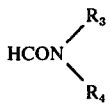

wherein $R_3$ and $R_4$ represent an aliphatic radical containing 1 to 20 carbon atoms.

Examples are N,N-dimethylformamide, N,N-diethylformamide, N,N-dipropylformamide, N,N-dibutylformamide, N,N-dihexylformamide, N,N-dioctylformamide, N,N-didecylformamide, N,N-didodecylformamide, N,N-dioctadecylformamide, N,N-dieicosylformamide, N-methyl-N-benzylformamide, and N-dodecyl-N-benzylformamide.

Preferred formyl derivatives of cyclic secondary amines are those of the general formula

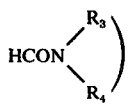

wherein $R_3 - R_4$ represents a biradical containing 3 to 20 carbon atoms.

Examples are N-formylpyrrolidine, N-formylpiperidine, N-formylmorpholine, N-formylthiamorpholine, N,N'-diformylpiperazine, N-formyl-N'-methylpiperazine, N-formylanabasine, N-formylindazole, N-formylimidazoline, N-formylpyrazoline, N-formylpurine, N-formylcarbazole, N-formylphenoxazine, N-formylindoline, and N-formylisoindoline.

The amount of the formyl derivative of a secondary amine is stoichiometrically excessive, preferably 2 to 50 mols, more preferably 3 to 10 mols, per mol of the carbonyl compound. The formyl derivative of a secondary amine not only acts as a starting material, but also serves as a solvent.

Preferred lower alcohols used in the process of this invention are lower aliphatic alcohols containing 1 to 4 carbon atoms. Methanol is especially preferred.

Preferred secondary amines used optionally together with water and/or a lower alcohol are the same secondary amines as constitute the starting formyl derivatives.

The amount of water and/or the lower alcohol may be optional, but preferably is 0.1 to 100 mols, more preferably 1 to 10 mols, per mol of the carbonyl compound. The amount of the secondary amine may be optional, but preferably is 0.01 to 10 mols, more preferably 0.1 to 5 mols, per mol of the carbonyl compound.

The reaction temperature used in the process of this invention is 100° to 350° C., preferably 150° to 300° C., more preferably 200° to 300° C. The reaction does not proceed at a temperature below 100° C. At a temperature of above 350° C., various side-reactions and decomposition reactions occur. The reaction proceeds at a favorable rate at a temperature of at least 150° C.

The reaction is carried out at a pressure at which the reaction mixture is maintained in the liquid phase. The reaction pressure can vary depending upon the partial pressures of the individual components of the reaction mixture, and the partial pressure of carbon dioxide gas generated, but usually is 5 to 300 kg/cm².guage. The carbon dioxide gas generated may be purged outside the reaction system during the reaction. The reaction time that can be employed in the invention is 5 to 50 hours.

The reaction may be carried out in the presence of a Lewis acid such as magnesium chloride as a catalyst, but even in its absence can give fully satisfactory results. The reaction may be carried out with stirring, but even without stirring, can give fully satisfactory results.

The reaction can be carried out either batchwise or continuously. The resulting tertiary amine can be recovered from the reaction mixture by any known procedures such as distillation, liquid-liquid separation, filtration or extraction with acids.

According to one embodiment of the process of this invention, a mixture comprising the water and/or alcohol, secondary amine, the excess of the formyl derivative, and unreacted carbonyl compound is directly used as a starting material. Since this mixture contains the secondary amine resulting from the decomposition of the formyl derivative of the secondary amine, the use of this recycle as a starting material leads to a marked reduction in the decomposition of the formyl derivative of secondary amine, and therefore, such a procedure is very advantageous and safe in industrial operations.

The carbonyl compound, one starting material in the process of this invention, is cheaper than the primary amine which is a starting material in the prior art, and the formyl derivative of a secondary amine, the other starting material, is more readily available and easy to handle. The process of this invention does not require a heterogeneous catalyst such as a hydrogenation catalyst used in the prior art, and enables the reaction to be performed without stirring. Accordingly, the process of this invention is very advantageous as an industrial process. The invention further has the advantage that there is no problem of equipment corrosion, and the tertiary amine can be obtained in very high yields.

The following Examples and Comparative Examples further illustrate the present invention, but needless to say, do not limit it in any way.

The conversion, selectivity, recovery ratio, decomposition ratio as used in these examples are defined as follows:

$$\text{Conversion (\%)} = \frac{\begin{pmatrix} \text{Mols of the} \\ \text{carbonyl} \\ \text{compound fed} \end{pmatrix} - \begin{pmatrix} \text{Mols of the un-} \\ \text{reacted carbonyl} \\ \text{compound} \end{pmatrix}}{\text{Mols of the carbonyl compound fed}} \times 100$$

$$\text{Selectivity (\%)} = \frac{\text{Mols of the tertiary amine produced}}{\begin{pmatrix} \text{Mols of the} \\ \text{carbonyl} \\ \text{compound fed} \end{pmatrix} - \begin{pmatrix} \text{Mols of the un-} \\ \text{reacted carbonyl} \\ \text{compound} \end{pmatrix}} \times 100$$

$$\text{Recovery ratio (\%)} = \frac{\text{Mols of the formyl derivative of secondary amine recovered}}{\begin{pmatrix}\text{Mols of the}\\\text{formyl deriva-}\\\text{tive of second-}\\\text{ary amine fed}\end{pmatrix} - \begin{pmatrix}\text{Mols of the}\\\text{tertiary}\\\text{amine}\\\text{produced}\end{pmatrix}} \times 100$$

Decomposition ratio (%) = 100 − recovery ratio

EXAMPLE 1

A 100 ml. stainless steel autoclave equipped with a stirrer was charged with 20.0 g of a ketone mixture having an average molecular weight of 200 and obtained by the oxidation of a saturated straight-chain hydrocarbon with 12 to 14 carbon atoms, 29.2 g of N,N-dimethylformamide, and 7.2 g of water, and they were reacted at 230° C. for 20 hours. The reaction pressure increased with the passage of time because of the formation of carbon dioxide gas, and reached 45.0 kg/cm².gauge in 20 hours. When the reaction system was cooled to room temperature, the pressure decreased to 13.5 kg/cm².gauge. There was obtained a reaction product divided into an upper layer (22.4 g) and a lower layer (28.3 g).

Analysis by gas-chromatography and amine titration showed that the upper layer consisted of 94.6% by weight of the desired secondary alkyl dimethylamine and the remainder being the unreacted ketone mixture. The conversion of the ketone mixture was 93.5%, and the selectivity to the secondary alkyl dimethylamine was 100%.

By the same analysis, the lower layer was found to be a mixture containing 19.1 g of N,N-dimethylformamide and 2.0 g of dimethylamine. The recovery ratio of the N,N-dimethylformamide was 85.4%, and therefore, its decomposition ratio was 14.6%.

EXAMPLE 2

The same autoclave as used in Example 1 was charged with 20.0 g of a ketone mixture having an average molecular weight of 200 and obtained by the oxidation of a saturated straight-chain hydrocarbon with 12 to 14 carbon atoms, 29.2 g of N,N-dimethylformamide, 7.2 g of water with 4.5 g of dimethylamine, and after purging the spatial part with nitrogen gas, they were heated at 230° C. for 20 hours. The reaction pressure increased with time because of the formation of carbon dioxide gas, and reached 56.2 kg/cm².gauge in 20 hours. When the reaction system was cooled to room temperature, the reaction pressure decreased to 15.5 kg/cm².gauge. There was obtained a reaction product divided into an upper layer (22.6 g) and a lower layer (33.6 g).

Analysis by gas-chromatography and amine titration showed that the upper layer consisted of 97.3% by weight of the desired secondary alkyl dimethylamine, and the remainder being the unreacted ketone mixture. The conversion of the ketone mixture was 97.0%, and the selectivity to the secondary alkyldimethylamine was 100%.

By the same analysis, the lower layer was found to be a mixture containing 21.6 g of N,N-dimethylformamide and 4.8 g of dimethylamine. The recovery ratio of N,N-dimethylformamide was 97.7%, and therefore, its decomposition ratio was 2.3%.

COMPARATIVE EXAMPLES 1 AND 2

The same autoclave as used in Example 1 was charged with 20.0 g of a ketone mixture having an average molecular weight of 200 and obtained by the oxidation of a saturated straight-chain hydrocarbon with 12 to 14 carbon atoms, and 29.2 g of N,N-dimethylformamide, and they were heated at 230° C. for 30 hours. No increase in pressure with time was observed. When the reaction system was cooled to room temperature, the reaction pressure was 0 kg/cm².gauge. The reaction product was obtained as a homogeneous phase, and its analysis by gas-chromatography and amine titration showed that the desired secondary alkyl dimethylamine was formed only in trace.

When the same reaction was carried out at 280° C. for 30 hours, the results were the same, and the desired secondary alkyl dimethylamine was obtained only in trace amounts.

The above results demonstrate that the reaction does not smoothly proceed in the absence of water.

EXAMPLE 3

The same procedure as in Example 1 was performed except that the reaction was carried out without stirring. The conversion of the ketone mixture, the selectivity to the secondary alkyl dimethylamine, and the decomposition ratio of N,N-dimethylformamide were much the same as in Example 1.

EXAMPLE 4

The same autoclave as used in Example 1 was charged with 10.0 g of a ketone mixture having an average molecular weight of 200 and obtained by the oxidation of a saturated straight-chain hydrocarbon with 12 to 14 carbon atoms, 14.6 g of N,N-dimethylformamide, and 6.4 g of methanol, and they were heated at 260° C. for 30 hours. The reaction pressure increased with time because of the formation of carbon dioxide gas, and reached 75.6 kg/cm².gauge in 30 hours. When the reaction system was cooled to room temperature, the reaction pressure decreased to 25.7 kg/cm².gauge.

Analysis of the reaction product by gas-chromatography and amine titration showed that the conversion of the ketone mixture was 92.6%, the selectivity of the secondary alkyl dimethylamine was 100%, and the decomposition ratio of N,N-dimethylformamide was 45.2%.

EXAMPLE 5

The same autoclave as used in Example 1 was charged with 10.0 g of a ketone mixture having an average molcular weight of 200 and obtained by the oxidation of a saturated straight-chain hydrocarbon with 12 to 14 carbon atoms, 14.6 g of N,N-dimethylformamide, 6.4 g of methanol and 9.0 g of dimethylamine, and they were heated at 260° C. for 30 hours. The reaction pressure increased with time because of the formation of carbon dioxide gas, and reached 60.4 kg/cm².gauge in 30 hours. When the reaction system was cooled to room temperature, the reaction pressure decreased to 14.7 kg/cm².gauge.

Analysis of the reaction product by gas-chromatography and amine titration showed that the conversion of the ketone mixture was 93.0%, the selectivity to the secondary alkyl dimethylamine was 100%, and the decomposition ratio of N,N-dimethylformamide was 25.6%.

EXAMPLE 6

The same autoclave as used in Example 1 was charged with 20.0 g of a ketone mixture having an average molecular weight of 200 and obtained by the oxidation of a saturated straight-chain hydrocarbon with 12 to 14 carbon atoms, 29.2 g of N,N-dimethylformamide, 6.3 g of water, 1.6 g of methanol and 4.5 g of dimethylamine, and they were heated at 230° C. for 20 hours. The reaction pressure increased with time because of the formation of carbon dioxide gas, and reached 57.3 kg/cm². gauge in 20 hours. When the reaction system was cooled to room temperature, the reaction pressure decreased to 15.0 kg/cm². gauge. There was obtained a reaction product divided into an upper layer (22.6) and a lower layer (34.3 g).

Analysis by gas-chromatography and amine titration showed that the upper layer was a mixture consisting of 97.3% by weight of the secondary alkyl dimethylamine and the remainder being the unreacted ketone mixture. The conversion of the ketone mixture was 97.0%, and the selectivity to the secondary alkyl dimethylamine was 100%.

By the same analysis, the lower layer was found to be a mixture containing 21.4 g of N,N-dimethylformamide and 5.0 g of dimethylamine. The recovery ratio of N,N-dimethylformamide was 96.8%, and its decomposition ratio was 3.2%.

EXAMPLE 7

The same autoclave as used in Example 1 was charged with 20.0 g of a ketone mixture having an average molecular weight of 200 and obtained by the oxidation of a saturated straight-chain hydrocarbon with 12 to 14 carbon atoms, 10.1 g of N,N-dimethylformamide and 28.3 g of the lower layer (containing 19.1 g of N,N-dimethylformamide and 2.0 g of dimethylamine) obtained in Example 1, and they were heated at 230° C. for 20 hours. The reaction pressure increased with time because of the formation of carbon dioxide gas, and reached 49.5 kg/cm².gauge in 20 hours. When the reaction system was cooled, the reaction pressure decreased to 15.0 kg/cm².gauge. There was obtained a reaction product divided into an upper layer (22.6 g) and a lower layer (30.7 g).

Analysis by gas-chromatography and amine titration showed that the upper layer was a mixture consisting of 97.3% of the secondary alkyl dimethylamine and the remainder being the unreacted ketone mixture. The conversion of the ketone mixture was 97.0%, and the selectivity to the secondary alkyl dimethylamine was 100%.

By the same analysis, the lower layer was found to be a mixture containing 21.0 g of N,N-dimethylformamide and 2.7 g of dimethylamine. The recovery ratio of N,N-dimethylformamide was 95.0%, and its decomposition ratio was 5.0%.

Then, the autoclave was charged with 20.0 g of the same ketone mixture as above, 30.7 g of the lower layer obtained above containing N,N-dimethylformamide and dimethylamine), and N,N-dimethylformamide in an amount required to adjust the total amount of N,N-dimethylformamide in the entire feed mixture to 29.2 g, and they were reacted in the same way as above. The above procedure was repeated 15 times using the lower layer as a recycle. As a result, the average conversion of the ketone mixture was 97.0%, and the selectivity to the secondary alkyl dimethylamine was 100%. On the other hand, the recovery ratio of N,N-dimethylformamide gradually increased from 95.0. After five operations, the recovery ratio reached 98.5%, and after ten operations, it became 99.0%. After 15 operations, the recovery ratio became almost constant at 99.2%. The decomposition ratio of N,N-dimethylformamide therefore became less than 1%.

EXAMPLES 8 and 9

A 2-liter stainless steel autoclave equipped with a reflux condenser and a pressure-maintaining valve was charged with 400 g of a ketone mixture having an average molecular weight of 200 and obtained by the oxidation of a saturated straight-chain hydrocarbon with 12 to 14 carbon atoms, 585 g of N,N-dimethylformamide, 144 g of water and 90 g of dimethylamine, and after purging the spatial part with nitrogen gas, they were heated at 230° C. for 20 hours without stirring. The reaction pressure increased because of the formation of carbon dioxide gas, but was maintained at 30 kg/cm².gauge by driving off the carbon dioxide gas outside the reaction system.

As a result of analyzing the reaction product by gas-chromatography and amine titration, it was confirmed that the conversion of the ketone mixture was 97.5%, the selectivity to the secondary alkyl dimethylamine was 100%, and the decomposition ratio of N,N-dimethylformamide was 2.0%.

When the above procedure was repeated except that dimethylamine was not used, the decomposition ratio of the N,N-dimethylformamide was 15.5%.

EXAMPLES 10 and 11

The same autoclave as used in Example 1 was charged with 9.8 g of cyclohexanone, 29.2 g of N,N-dimethylformamide, 7.2 g of water and 4.5 g of dimethylamine, and they were heated at 230° C. for 20 hours. The reaction pressure increased with time, and reached 53.3 kg/cm².gauge in 20 hours. When the reaction system was cooled to room temperature, the reaction pressure decreased to 13.8 kg/cm².gauge.

Analysis of the reaction product by gas-chromatography and amine titration showed that the conversion of cyclohexanone was 98.5%, the selectivity to the cyclohexyl dimethylamine was 100%, and the decomposition ratio of N,N-dimethylformamide was 2.1%.

When the above procedure was repeated except that dimethylamine was not used, the decomposition ratio of N,N-dimethylformamide was 14.3%.

COMPARATIVE EXAMPLE 3

The same autoclave as used in Example 1 was charged with 9.8 g of cyclohexanone and 29.2 g of N,N-dimethylformamide, and they were heated at 240° C. for 30 hours in the absence of water. No increase in pressure with time was observed, and When the reaction system was cooled to room temperature, the reaction pressure decreased to 0 kg/cm².gauge.

A gas-chromatographic analysis of the reaction product showed that the desired N,N-dimethyl cyclohexylamine was obtained in trace amounts.

EXAMPLES 12 and 13

The same autoclave as used in Example 1 was charged with 12.0 g of acetophenone, 29.2 g of N,N-dimethylformamide, 7.2 g of water and 4.5 g of dimethylamine, and they were heated at 230° C. for 15 hours. The reaction pressure increased with time because of the formation of carbon dioxide gas, and reached 52.5 kg/cm². gauge in 15 hours. When the reaction system was cooled to room temperature, the reaction pressure decreased to 10.1 kg/cm².gauge.

Analysis of the reaction product by gas-chromatography and amine titration showed that the conversion of acetophenone was 98.3%, the selectivity of the α-phenetyl dimethylamine was 100%, and the decomposition ratio of N,N-dimethylformamide was 2.1%.

When the above procedure was repeated except that dimethylamine was not used, the decomposition ratio of the N,N-dimethylformamide was 14.1%.

EXAMPLE 14

The same autoclave as used in Example 1 was charged with 18.2 g of benzophenone, 29.2 g of N,N-dimethylformamide and 7.2 g of water, and they were heated at 240° C. for 24 hours. The reaction pressure increased with time because of the formation of carbon dioxide gas, and reached 48.4 kg/cm².gauge in 24 hours. When the reaction system was cooled to room temperature, the pressure decreased to 14.7 kg/cm².gauge.

Analysis of the reaction product by gas-chromatography and amine titration showed that the conversion of benzophenone was 97.0%, the selectivity to N,N-dimethyl benzohydrylamine was 100%, and the decomposition ratio of N,N-dimethylformamide was 16.3%.

EXAMPLES 15 and 16

The same autoclave as in Example 1 was charged with 12.8 g of n-octylaldehyde, 29.2 g of N,N-dimethylformamide and 7.2 g of water, and they were reacted at 220° C. for 20 hours. The reaction pressure increased with time because of the formation of carbon dioxide gas, and reached 44.0 kg/cm².gauge in 20 hours. When the reaction system was cooled to room temperature, the reaction pressure decreased to 14.0 kg/cm².gauge.

The reaction product formed two separate layers. Analysis of the upper layer (14.5 g) by gas-chromatography and amine titration showed that the conversion of n-octylaldehyde was 100%, the selectivity to n-octyldimethylamine was 68.0%, and the decomposition ratio of N,N-dimethylformamide was 17.1%.

The same autoclave as used above was charged with 18.4% of n-dodecylaldehyde, 29.2 g of N,N-dimethylformamide and 7.2 g of water, and they were heated at 200° C. for 20 hours in the same way as above. The results were much the same. The conversion of n-dodecylaldehyde was ±100%, the selectivity to n-dodecyl dimethylamine was 69.4%, and the decomposition ratio of N,N-dimethylformamide was 16.8%.

EXAMPLES 17 and 18

The same autoclave as used in Example 1 was charged with 12.8 g of 2-ethylhexylaldehyde, 29.2 g of N,N-dimethylformamide, 7.2 g of water and 4.5 g of dimethylamine and they were heated at 220° C. for 20 hours. The reaction pressure increased with time because of the formation of carbon dioxide gas, and reached 50.1 kg/cm².gauge in 20 hours. When the reaction system was cooled to room temperature, the reaction pressure decreased to 14.3 kg/cm².gauge.

Analysis of the reaction product by gas-chromatography and amine titration showed that the conversion of 2-ethylhexylaldehyde was 94.8%, the selectivity to 2-ethylhexyl dimethylamine was 97.0%, and the decomposition ratio of N,N-dimethylformamide was 4.6%.

When the above procedure was repeated without using dimethylamine, the conversion of 2-ethylhexylaldehyde was 94.5%, the selectivity to 2-ethylhexyl dimethylamine was 96.7%, and the decomposition ratio of N,N-dimethylformamide was 16.5%.

EXAMPLE 19

The same autoclave was used in Example 1 was charged with 12.8 g of 2-ethylhexylaldehyde, 29.2 g of N,N-dimethylformamide, and 12.8 g of methanol, and they were reacted at 240° C. for 20 hours. The reaction pressure increased with time because of the formation of carbon dioxide gas, and reached 46.2 kg/cm². gauge in 20 hours. When the reaction system was cooled to room temperature, the reaction pressure decreased to 10.6 kg/cm².gauge.

The reaction product was obtained as a homogeneous phase. Analysis of the reaction product by gas-chromatography and amine titration showed that the conversion of 2-ethylhexylaldehyde was 90.7%, the selectivity to 2-ethylhexyldimethylamine was 93.1%, and the decomposition ratio of N,N-dimethylformamide was 42.6%.

EXAMPLE 20

The same autoclave as used in Example 1 was charged with 11.2 g of cyclohexanealdehyde, 29.2 g of N,N-dimethylformamide, 7.2 g of water and 4.5 g of dimethylamine, and they were heated at 220° C. for 20 hours. The reaction pressure increased with time because of the formation of carbon dioxide gas, and reached 40.3 kg/cm².gauge in 20 hours. When the reaction system was cooled to room temperature, the reaction pressure decreased to 7.3 kg/cm². gauge.

Analysis of the reaction product by gas-chromatography and amine titration showed that the conversion of cyclohexanealdehyde was 100%, the selectivity to N,N-dimethylamino methylcyclohexane was 99.0%, and the decomposition ratio of the N,N-dimethylformamide was 3.2%.

EXAMPLES 21 and 22

The same autoclave as used in Example 1 was charged with 13.3 g of a ketone mixture having an average molecular weight of 200 and obtained by the dehydrogenation of a secondary alcohol with 12 to 14 carbon atoms, 30.7 g of N-formylmorpholine, 4.8 g of water and 8.7 g of morpholine, and they were reacted at 240° C. for 20 hours. The reaction pressure increased with time because of the formation of carbon dioxide gas, and reached 45.8 kg/cm².gauge in 20 hours. When the reaction system was cooled to room temperature, the reaction pressure reached 14.0 kg/cm².gauge.

Analysis of the reaction product by gas-chromatography and amine titration showed that the conversion of the ketone mixture was 97.0%, the selectivity to N-sec.

alkyl morpholine was 97.8%, and the decomposition ratio of N-formylmorpholine was 1.6%.

When the above procedure was repeated without using morpholine, the decomposition ratio of N-formylmorpholine was 15.8%.

EXAMPLES 23 and 24

The same autoclave as used in Example 1 was charged with 10.6 g of benzaldehyde, 45.2 g of N-formyl piperidine, 7.2 g of water and 8.5 g of piperidine, and they were heated at 220° C. for 15 hours. The reaction pressure increased with time because of the formation of carbon dioxide gas, and reached 43.3 kg/cm². gauge in 15 hours. When the reaction system was cooled to room temperature, the reaction pressure decreased to 12.7 kg/cm².gauge.

Analysis of the reaction product by gas-chromatography and amine titration showed that the conversion of benzaldehyde was 99.0%, the selectivity to N-benzylpiperidine was 98.8%, and the decomposition ratio of N-formylpiperidine was 1.2%.

When the above procedure was repeated without using piperidine, the decomposition ratio of N-formyl piperidine was 13.6%.

What we claimed is:

1. A process for preparing tertiary amines which comprises in absence of added formic acid reacting a carbonyl compound with a formyl derivative of a secondary amine at a temperature of 200° to 300° C. in the presence of at least one compound selected from the group consisting of water and lower aliphatic alcohols containing 1 to 4 carbon atoms, the amount of said at least one compound selected from the group consisting of water and lower alcohols containing 1 to 4 carbon atoms being 1 to 10 mols per mol of the carbonyl compound, said carbonyl compound being selected from the group consisting of:

1. aliphatic aldehydes of the general formula

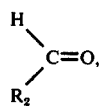

wherein $R_2$ is an aliphatic radical containing 1 to 40 carbon atoms, 2. alicyclic aldehydes of the general formula

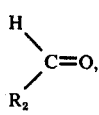

wherein $R_2$ is an alicyclic radical containing 5 to 20 carbon atoms, 3. aromatic aldehydes of the general formula

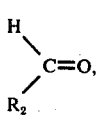

wherein $R_2$ is an aromatic radical, 4. aliphatic ketones of the general formula

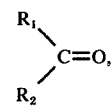

wherein $R_1$ and $R_2$ represent an aliphatic radical containing 1 to 20 carbon atoms, 5. aliphatic-aromatic ketones of the general formula

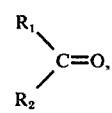

wherein $R_1$ is an aliphatic radical containing 1 to 20 carbon atoms and $R_2$ is an aromatic radical, 6. aliphatic-heterocyclic ketones of the general formula

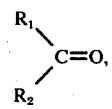

wherein $R_1$ is an aliphatic radical containing 1 to 20 carbon atoms and $R_2$ is a heterocyclic radical, 7. aromatic ketones of the general formula

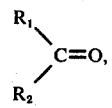

wherein $R_1$ and $R_2$ represent an aromatic radical, and 8. alicyclic ketones of the general formula

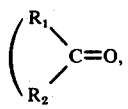

wherein $R_1$–$R_2$ is a biradical containing 4 to 40 carbon atoms, said formyl derivative of a secondary amine being selected from i. formyl derivatives of aliphatic secondary amines of the general formula

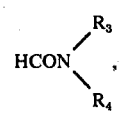

wherein $R_3$ and $R_4$ represent an aliphatic radical containing 1 to 20 carbon atoms, and ii. formyl derivatives of cyclic secondary amines of the general formula

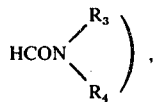

wherein R₃–R₄ represents a biradical containing 3 to 20 carbon atoms, all of said aliphatic and alicyclic radicals and alcohols being saturated.

2. A process of claim 1 wherein a secondary amine is present at the start of the reaction, said secondary amine being the same as that present as the formyl derivative.

3. A process according to claim 1 wherein an aliphatic aldehyde is employed as the carbonyl compound and said aldehyde is selected from the group consisting of ethanal, propanal, butanal, pentanal, hexanal, heptanal, octanal, nonanal, decanal, undecanal, dodecanal, tridecanal, tetradecanal, pentadecanal, hexadecanal, heptadecanal, octadecanal, nonadecanal, eicosanal, heneicosanal, docosanal, tricosanal, tetracosanal, pentacosanal, hexacosanal, heptacosanal, octacosanal, nonacosanal, triacontanal, hentriacontanal, ditriacontanal, tritriacontanal, tetratriacontanal, pentatriacontanal, hexatriacontanal, heptatriacontanal, octatriacontanal, nonatriacontanal, tetracontanal hentetracontanal, pentanedial, hexanedial, octanedial, decanedial, dodecanedial, straight chain oxoaldehydes obtained by the oxo-reaction of stright-chain monolefins containing 10 to 40 carbon atoms; 2-methylpropanal, 2-methylbutanal, 2-methylpentanal, 2-methylhexanal, 2-methylheptanal, 2-methyloctanal, 2-methylnonanal, 2-methyldecanal, 2-methylundecanal, 2-methyldodecanal, 2-methyltridecanal, 2-methyltetradecanal, 2-methylpentadecanal, 2-methylhexadecanal, 2-methylheptadecanal, 2-methyloctadecanal, 2-methylnonadecanal, 2-methyleicosanal, 2,2-dimethylpropanal, 2-ethylbutanal, 2-ethylhexanal, 2-propylheptanal, 2-butyloctanal, 2-pentylnonanal, 2-hexyldecanal, 2-octyldodecanal and 2-methyloxoaldehyde mixtures obtained by the oxo-reaction of straight-chain monolefins containing 10 to 40 carbon atoms.

4. A process according to claim 1 wherein an alicyclic aldehyde is employed as the carbonyl compound and said aldehyde is selected from the group consisting of cyclopentane-aldehyde, cyclohexane-aldehyde, cycloheptane-aldehyde, cyclooctane-aldehyde, cyclodecane-aldehyde, cyclododecanealdehyde, cyclononadecane-aldehyde, cyclohexane-1,2-dialdehyde, cyclohexane-1,3-dialdehyde, cyclohexane-1,4-dialdehyde, 2-methylcyclohexane-aldehyde, 3-methylcyclohexane-aldehyde, 4-methylcyclohexane-aldehyde, and 4-methoxycyclohexane-aldehyde.

5. A process according to claim 1 wherein an aromatic aldehyde is employed as the carbonyl compound and said aldehyde is selected from the group consisting of benzaldehyde, o-phthalic aldehyde, m-phthalic aldehyde, p-phthalic aldehyde, α-naphthoic aldehyde, β-napththoic aldehyde, o-tolualdehyde, m-tolualdehyde, p-tolualdehyde, o-anisaldehyde, m-anisaldehyde, p-anisaldehyde, o-chlorobenzaldehyde, m-chlorobenzaldehyde, p-chlorobenzaldehyde, o-bromobenzaldehyde, m-bromobenzaldehyde, p-bromobenzaldehyde, 2,4-dimethoxybenzaldehyde, 3,4-dimethoxybenzaldehyde, o-nitrobenzaldehyde, m-nitrobenzaldehyde, p-nitrobenzaldehyde, p-dimethylaminobenzaldehyde, and cumic aldehyde.

6. A process according to claim 1 wherein an aliphatic ketone is employed as the carbonyl compound and said ketone is selected from the group consisting of 2-propanone, 2-butanone, pentanones, hexanones, heptanones, octanones, nonanones, decanones, undecanones, dodeconones, tridecanones, tetradecanones, pentadecanones, hexadecanones, heptadecanones, octadecanones, nonadecanones, eicosanones, heneisosanones, docosanones, tricosanones, tetracosanones, pentacosanones, hexacosanones, heptacosanones, octacosanones, nonacosanones, triacontanones, hentriacontanones, dotriacontanones, tritriacontanones, tetratriacontanones, pentatriacontanones, hexatriacontanones, heptatriacontanones, octatriacontanones nonatriacontanones, tetracontanones, hentetracontanones, 4-methyl-2-pentanone, 2,4-dimethyl-3-pentanone, 2,6-dimethyl-4-heptanone, 1-phenyl-2-propanone, 1-(o-chloro)-phenyl-2-propanone, 1-(m-nitro)-phenyl-2-propanone, methyl cyclohexyl ketone, ketone mixtures obtained by the oxidation of straight chain hydrocarbons containing 10 to 40 carbon atoms, and ketone mixtures obtained by the dehydrogenation of secondary alcohols containing 10 to 40 carbon atoms.

7. A process according to claim 1 wherein an aliphatic aromatic ketone is employed as the carbonyl compound and said ketone is selected from the group consisting of acetophenone, propionphenone, isobutyrophenone, isovalerophenone, laurophenone, β-acetonaphthone, p-chloroacetophenone, p-bromoacetophenone, p-methoxyacetophenone, p-methylacetophenone, m-nitroacetophenones, p-phenoxyacetophenone, and p-phenylacetophenone.

8. A process according to claim 1 wherein an aliphatic heterocylic ketone is employed and said ketone is selected from the group consisting of α-acetothienone and α-propiothenone.

9. A process according to claim 1 wherein an aromatic ketone is employed and said ketone is selected from the group consisting of benzophenone and fluorenone.

10. A process according to claim 1 wherein an alicyclic ketone is employed and said ketone is selected from the group consisting of cyclopentanone, cyclohexanone, cycloheptanone, cyclooctanone, cyclodecanone, cyclododecanone, cyclopentadecanone, fenchone, menthone, 2-camphanone, 3-cholestanone, thujone, 2-methylcyclopentanone, 3-methylcyclopentanone, 2-methylcyclohexanone, 3-methylcyclohexanone, and 4-methylcyclohexanone.

11. A process according to claim 1 wherein a formyl derivative of a aliphatic secondary amine is employed and said derivative is selected from the group consisting of N,N-dimethylformamide, N,N-diethylformamide, N,N-dipropylformamide, N,N-dibutylformamide, N,N-dihexylformamide, N,N-dioctylformamide, N,N-didecylformamide, N,N-didodecylformamide, N,N-dioctadecylformamide, N,N-dieicosylformamide, N-methyl-N-benzylformamide, and N-dodecyl-N-benzylformamide.

12. A process according to claim 1 wherein a formyl derivative of a cyclic secondary amine is employed and said derivative is selected from the group consisting of N-formylpyrrolidine, N-formylpiperidine, N-formylmorpholine, N-formylthiamorpholine, N,N'-diformylpiperazine, N-formyl-N'-methylpiperazine, N-formylanabasine, N-formylindazole, N-formylimidazoline, N-formylpyrazoline, N-formylpurine, N-formylcarbazole, N-formylphenoxazine, N-formylindoline, and N-formylisoindoline.

13. The process of claim 1 wherein said lower alcohol is methanol.

14. The process of claim 2 wherein said lower alcohol is methanol.

15. The process of claim 2 wherein said secondary amine is an aliphatic secondary amine.

16. The process of claim 2 wherein said secondary amine is a cyclic secondary amine.

* * * * *